United States Patent [19]

McCarthy

[11] Patent Number: 5,160,047
[45] Date of Patent: Nov. 3, 1992

[54] GLUTARALDEHYDE FOR CONTROLLING ZEBRA MUSSELS

[75] Inventor: Robert E. McCarthy, Naperville, Ill.

[73] Assignee: Nalco Chemical Company, Naperville, Ill.

[21] Appl. No.: 836,473

[22] Filed: Feb. 18, 1992

[51] Int. Cl.$^5$ .............................................. C02F 1/50
[52] U.S. Cl. ................................ 210/749; 210/764; 422/7; 422/36; 514/693; 514/705
[58] Field of Search ................ 210/749, 764, 698; 422/7, 36; 514/693, 694, 705

[56] References Cited

U.S. PATENT DOCUMENTS

| | | | |
|---|---|---|---|
| 5,015,395 | 5/1991 | Muia et al. | 210/755 |
| 5,062,967 | 11/1991 | Muia et al. | 210/755 |
| 5,096,601 | 3/1992 | Muia et al. | 210/755 |

FOREIGN PATENT DOCUMENTS 55041 12/1985 Japan.

OTHER PUBLICATIONS

Trulear, M., et al., "Macro Fouling Control", Nalco Reprint No. 533, Dec. 1990.
Bretz, E., Zebra Mollusks: A Danger of a Different Shape, Elec. World, Dec. 1990 pp. 72-74.

Primary Examiner—Stanley S. Silverman
Assistant Examiner—Neil M. McCarthy
Attorney, Agent, or Firm—John G. Premo; Robert A. Miller; Joseph B. Barrett

[57] ABSTRACT

Glutaraldehyde is effective in controlling Zebra mussels found in industrial process waters.

2 Claims, No Drawings

GLUTARALDEHYDE FOR CONTROLLING ZEBRA MUSSELS

SUMMARY OF THE INVENTION

Glutaraldehyde is effective in controlling Zebra mussels comtaminating industrial process waters.

BACKGROUND OF THE INVENTION

*D. polymorpha*, the Zebra mussel, has just recently been introduced to North America. *D. polymorpha* was first discovered in June, 1988 in Lake St. Clair and is thought to have been introduced into the region in 1986 by fresh water ballast discharge from an ocean-going ship. Since its introduction, *D. polymorpha* has spread rapidly throughout Lake Erie and into western Lake Ontario. Scattered populations have now been found in all five Great Lakes. Native to the Black and Caspian Seas, *D. polymorpha* rapidly spread throughout Europe and the Soviet Union during the past two centuries and is expected to soon be a major macrofouling pest in fresh waters throughout the United States.

Common to bivalve molluscs, fouling by Zebra mussel occurs primarily as a result of larvae transport into plant systems by water currents, settlement of the larvae in low flow areas, and subsequent growth of the organism to sizes large enough to impair system operation.

Zebra mussel larvae and juveniles aggressively attach to all types of hard surfaces including intake structures, screens, pipes, and other mussel shells, to form dense thick layers of mussel accumulations. Pipeline surfaces can be entirely encrusted by Zebra mussel shells, impeding flow and accelerating corrosion. Clusters and massive mats of mussel shells can break off and become entrained back in the fluid flow, causing equipment plugging and additional fouling problems.

The literature is replete with summaries of the problems occasioned by Zebra mussel fouling of surfaces in contact with industrial process waters, particularly industrial cooling waters. Two such summaries are: "Macrofouling Control", by M. G. Trulear et al., Nalco Reprint No. 533, December 1990., and "Zebra Mollusks: A Danger of a Different Shape", Bretz, E., Electrical World December 1990, pages 72-74. The disclosure of these articles is incorporated herein by reference.

THE INVENTION

A method for controlling the macrofouling by zebra mussels of surfaces in contact with industrial process waters which contain zebra mussels which comprises treating these waters with a zebra mussel controlling amount of glutaraldehyde.

In a preferred embodiment of the invention the glutaraldehyde is remarkably effective in controlling zebra mussels in industrial cooling waters.

The effective dosage may vary between about 5 to 50 parts per million, (ppm) on a weight basis, of glutaraldehyde added to the industrial process water infested with the zebra mussels. A usually effective dosage is between 10 to 25 ppm. The dosage may vary depending upon circumstances. Slug or continuous feed techniques may be used.

In comparison to other Zebra mussel control agents, glutaraldehyde is a relatively fast acting agent with a long half-life. At pH 7.0 and 25° C., glutaraldehyde has a half-life of 300 days. Glutaraldehyde has also been documented to remove biofilms which appear to be important for establishment of settled zebra mussel veligers. The concentration of this invention can be easily monitored with available test methods. A significant amount of environmental and toxicological data has been collected on this molecule. Also, there are methods available for chemical inactivation of this molecule.

It has long been established that glutaraldehyde is an effective microbiocide. Glutaraldehyde is an effective killing agent against bacteria and has been used as such in numerous applications. However, its potential effectiveness against macrofouling organisms, such as the Zebra mussel is unknown. Therefore, a series of experiments were conducted to evaluate its utility as a Zebra mussel control agent.

EVALUATION OF THE INVENTION

A series of recirculating test buckets (3L) was used to assay Zebra mussel mortality. Adult Zebra mussels (25) were placed in conditions with synthetic cooling water (150 ppm Ca, 75 ppm Mg, and 110 ppm "M" alkalinity, pH 8.2-8.3) before initiation of the experiment. During the acclimation period, the mussels typically become attached to the bottom of the test bucket. After the acclimation period, delivery of the glutaraldehyde was initiated to each test bucket. The working solution of glutaraldehyde was prepared from a 15% stock solution of Aquacar 515 (Union Carbide). A 1500 ppm (active) solution of glutaraldehyde was prepared and placed in 60 cc disposable syringes and positioned on Harvard syringe pumps. Chemical was fed to each test bucket on a continuous basis over a several day time period. The actual glutaraldehyde concentration in each test bucket was determined each day with the Aquacar field test kit. Test buckets were scored each day for the number of effete zebra mussels. A negative control test bucket (received no chemical treatment) was run with each experiment. Two different concentrations of glutaraldehyde were assayed for effectiveness. The results of 2 independent experiments are shown below in Tables 1 and 2.

TABLE 1

|  | Day No. | 7.7 ppm Glutaraldehyde Average concentration* | 23.5 ppm Glutaraldehyde |
| --- | --- | --- | --- |
| % Cumulative Mortality | 1 | 0 | 0 |
|  | 2 | 0 | 0 |
|  | 3 | 5% | 30% |
|  | 4 | 10% | 70% |
|  | 5 | 15% | 75% |
|  | 6 | 20% | 90% |
|  | 7 | 25% | 95% |
|  | 8 | 35% | 100% |

*These two glutaraldehyde concentrations are the average concentration of glutaraldehyde over the course of the experiment. The % cumulative mortality in the control test system was 15%.

TABLE 2

|  | Day # | 21.4 ppm Glutaraldehyde | 23.6 ppm Glutaraldehyde | 10.1 Glutaraldehyde |
| --- | --- | --- | --- | --- |
| % Cumulative Mortality | 1 | 0 | 0 | 12% |
|  | 2 | 8% | 8% | 16% |
|  | 3 | 32% | 32% | 24% |
|  | 4 | 88% | 76% | 48% |
|  | 5 | 96% | 88% | 72% |
|  | 6 | 100% | 92% | 80% |
|  | 7 | 100% | 96% | 88% |
|  | 8 | 100% | 100% | 88% |

Based on the results of these 2 independent experiments, it would appear that relatively low concentrations of glutaraldehyde may be effective against Zebra mussels. The possible mode of action of glutaraldehyde is:

(a) cross-linking the adductor muscle proteins which allow the mussel to regulate opening and closing of the valves; or, (b) is disrupting normal functioning of the proteins at the gill epithelial surface which are important for oxygen exchange.

I claim:

1. A method for controlling macrofouling caused by the attachment of Zebra mussels to surfaces in contact with industrial process waters which contain Zebra mussels which comprises treating these waters with from 5 to 50 parts per million of glutaraldehyde.

2. The method of claim 1 where the industrial process water is a cooling water.

* * * * *